US009649299B2

(12) United States Patent
Yeritsyan

(10) Patent No.: US 9,649,299 B2
(45) Date of Patent: May 16, 2017

(54) TRANSDERMAL PARASITICIDAL FORMULATIONS

(71) Applicant: DONAGHYS LIMITED, Christchurch (NZ)

(72) Inventor: Karen Yeritsyan, Dunedin (NZ)

(73) Assignee: Donaghys Limited, Christchurch (NZ)

( * ) Notice: Subject to any disclaimer, the term of this patent is extended or adjusted under 35 U.S.C. 154(b) by 0 days.

(21) Appl. No.: 14/742,622

(22) Filed: Jun. 17, 2015

(65) Prior Publication Data

US 2015/0283119 A1 Oct. 8, 2015

Related U.S. Application Data

(63) Continuation of application No. PCT/NZ2013/000235, filed on Dec. 16, 2013.

(30) Foreign Application Priority Data

Dec. 18, 2012 (NZ) .................................... 604848
Feb. 12, 2013 (NZ) .................................... 606938

(51) Int. Cl.

| | |
|---|---|
| ***A61K 31/429*** | (2006.01) |
| ***A61K 47/14*** | (2017.01) |
| ***A61K 9/00*** | (2006.01) |
| ***A61K 31/175*** | (2006.01) |
| ***A61K 31/365*** | (2006.01) |
| ***A61K 31/53*** | (2006.01) |
| ***A61K 31/7048*** | (2006.01) |
| ***A01N 35/02*** | (2006.01) |
| ***A01N 43/90*** | (2006.01) |
| ***A61K 45/06*** | (2006.01) |
| ***A61K 9/08*** | (2006.01) |

(52) U.S. Cl.

CPC ............ *A61K 31/429* (2013.01); *A01N 35/02* (2013.01); *A01N 43/90* (2013.01); *A61K 9/0017* (2013.01); *A61K 9/08* (2013.01); *A61K 31/175* (2013.01); *A61K 31/365* (2013.01); *A61K 31/53* (2013.01); *A61K 31/7048* (2013.01); *A61K 45/06* (2013.01); *A61K 47/14* (2013.01)

(58) Field of Classification Search

None

See application file for complete search history.

(56) References Cited

U.S. PATENT DOCUMENTS 4,096,262 A * 6/1978 Andrews
6,933,318 B1 8/2005 Kassebaum et al.

FOREIGN PATENT DOCUMENTS

| | | |
|---|---|---|
| EP | 249409 | 12/1987 |
| NZ | 336139 | 7/2002 |
| NZ | 507445 | 3/2003 |
| NZ | 517227 | 4/2003 |
| WO | WO-02/094221 | 11/2002 |
| WO | WO 2004/089239 A2 * | 10/2004 |
| WO | WO-2009/002809 | 12/2008 |
| WO | WO-2009/117621 | 9/2009 |
| WO | WO-2014/098619 | 6/2014 |

OTHER PUBLICATIONS

International Search Report and Written Opinion for PCT/NZ2013/000235, mailed May 6, 2014, 10 pages.

International Preliminary Report on Patentability for PCT/NZ2013/000235, mailed Dec. 18, 2012, 12 pages.

* cited by examiner

*Primary Examiner* — Savitha Rao
*Assistant Examiner* — Gregg Polansky
(74) *Attorney, Agent, or Firm* — Morrison & Foerster LLP

(57) ABSTRACT

Described herein are transdermal parasiticidal formulations and methods of treatment and use, wherein the formulation is not only able to deliver an agent or agents through the skin layer, but is able to do so through wool, dirt and/or a sebum layer on the skin if such layers are present. The transdermal parasiticidal formulation may be a solution including a therapeutically effective amount of levamisole anthelmintic agent dissolved in a solution including isopropyl myristate and D-limonene. This base formulation is highly compatible with other compounds and various other actives may be added to this formulation.

30 Claims, No Drawings

TRANSDERMAL PARASITICIDAL FORMULATIONS

CROSS REFERENCE TO RELATED APPLICATIONS

This application is a continuation of International Application No. PCT/NZ2013/000235, filed on Dec. 16, 2013 and claims priority to and the benefit of New Zealand Patent Application Nos. NZ604848 filed on Dec. 18, 2012, and NZ606938 filed on Feb. 12, 2013, the entire contents each of which are incorporated herein by reference in their entirety.

TECHNICAL FIELD

Described herein are transdermal parasitical formulations. Methods of treatment and use of the formulations are also described.

BACKGROUND ART

Transdermal vehicle formulations are known and used for delivery of a variety of active agents. In veterinary applications, such formulations are often referred to as ‘pour on’ treatments. The transdermal route of administration is favourable as it minimises the amount of work required to deliver an agent or agents to an animal and avoids potential harm or danger in handling distressed animals. A further advantage of transdermal administration is that the dose can easily be metered, measured and delivered to the animal.

Despite the above advantages, transdermal methods of administration are rarely commercialised for use with woolly animals such as sheep and goats. This is because such animals present a major challenge for transdermal delivery as it is necessary to penetrate through not only the skin or epidermis but also diffuse the active agent through wool, dirt that is usually present on the wool, and then to also penetrate the sebum—mainly comprising lanolin in woolly animals. Lanolin is a highly difficult waxy substance to penetrate as it is highly immiscible with water and repels most agents and vehicle systems.

Art exists describing transdermal formulations for treatment of internal and external parasites in animals where different active ingredients from anthelmintic range are used. However, with the exception of cattle pour on’s, few other pour on formulations have been commercialised and there remains a demand for a parasiticidal topically applied product, particularly for animals other than cattle.

Attempts have been made to develop reliable transdermal formulations suitable for woolly animal application, particularly for sheep and goats. These formulations typically have significant limitations in application timing and method. One example of an art composition commercialised in Australia is produced by Coopers, marketed under the brand Maverick™. This product is an endo-parasite transdermal formulation. The product has a number of limitations hence the uptake by the market has not been big with most farmers still preferring the difficulties of drenching sheep as opposed to using the Maverick™ product. By way of example, the Maverick™ product is recommended to be used only within 24 hours of shearing thereby severely limiting the window of application time. Further, a special applicator gun is needed in order to administer Maverick™. This greatly increases the cost and complexity to the farmer in using the product. The Maverick™ product is also a specialised micellar formulation that may require special manufacture and potentially expensive compounds to manufacture.

Further, as may be appreciated, it can be useful to combine two or more active agents in the one formulation. This can further complicate the formulation process for pour on design (for woolly and non-woolly animals) as different agents may have different characteristics such as varying miscibility. Patents that describe potential solutions to formulating multiple agents together include: NZ336139 that describes levamisole in an emulsion with ivermectin and albendazole and NZ507445 that describes a composition containing an antibiotic and an anthelmintic compound in the form of a suspension.

Production of emulsions or suspensions is not ideal since preparation of products containing different phases, such as solid/liquid or oil/water phases can be associated with significant manufacturing costs. For example, high shear dispensers and/or mills or homogenisers may be needed to produce the end product. Further, emulsions and suspensions can settle during storage and require the user to for example shake the product to re-suspend or, in worst cases, the agents will not re-mix resulting in ineffective products. In some cases, separation issues can result in short product storage time periods thereby limiting the usefulness of the product.

As should be appreciated from the above, there may be value in providing transdermal formulations that are simple to manufacture; minimise the amount of excipients used; are able to penetrate the skin barrier in an efficacious manner; deliver the agent or agents in a measurable and easily applied manner; and be able to deal with challenging conditions when the skin also has wool, dirt or sebum fats, oils or waxes present; or at least to provide the public with a choice.

Further aspects and advantages of the formulations, methods of treatment and use will become apparent from the ensuing description that is given by way of example only.

SUMMARY

Described herein are transdermal parasiticidal formulations and methods of treatment and use, wherein the formulation is not only able to deliver an agent or agents through the skin layer, but is able to do so through wool, dirt and/or a sebum layer on the skin if such layers are present.

In a first aspect there is provided a transdermal parasiticidal formulation in the form of a solution including a therapeutically effective amount of levamisole anthelmintic agent dissolved in a solution including isopropyl myristate and D-limonene.

In a second aspect, there is provided a transdermal parasiticidal formulation in the form of a solution including:

(a) a therapeutically effective amount of levamisole anthelmintic agent dissolved in a solution including isopropyl myristate and D-limonene;
(b) at least one diethylene glycol ether (DGE) compound;
(c) a penetrating agent or agents selected from at least one non-ionic surfactant;
(d) at least one preservative; and
(e) at least one diluent.

In a third aspect there is provided a dual active anthelmintic formulation formulated for transdermal administration including:

(a) a therapeutically effective amount of levamisole anthelmintic agent dissolved in a solution including isopropyl myristate and D-limonene;

(b) a therapeutically effective amount of at least one macrocyclic lactone dissolved in at least one diethylene glycol ether (DGE) compound;

(c) a penetrating agent or agents selected from at least one non-ionic surfactant;

(d) at least one preservative; and (e) at least one diluent.

In a fourth aspect there is provided a method of treatment of a condition and/or disease in an animal by administration of a composition substantially as described above.

In a fifth aspect there is provided the use of a formulation substantially as described above along with at least one active agent in the manufacture of a composition formulated for transdermal administration in the treatment of a condition and/or disease.

Advantages of the formulations, simplicity of manufacturing, methods of treatment, and uses thereof should be apparent including the ability to penetrate the epidermis in an effective manner even when the skin is covered by wool, dirt and sebum barriers such as oils, waxes and fats. A yet further advantage is that the formulation described maintains a viscosity sufficiently low to allow for accurate administration by pouring or spot application of the formulation to an animal.

DETAILED DESCRIPTION

As noted above, described herein are transdermal parasiticidal formulations and methods of treatment and use, wherein the formulation is not only able to deliver an agent or agents through the skin layer, but is able to do so through wool, dirt and/or a sebum layer on the skin if such layers are present.

For the purposes of this specification, the term 'about' or 'approximately' and grammatical variations thereof mean a quantity, level, degree, value, number, frequency, percentage, dimension, size, amount, weight or length that varies by as much as 30, 25, 20, 15, 10, 9, 8, 7, 6, 5, 4, 3, 2, or 1% to a reference quantity, level, degree, value, number, frequency, percentage, dimension, size, amount, weight or length.

For the purpose of this specification the term 'comprise' and grammatical variations thereof shall have an inclusive meaning—i.e. that it will be taken to mean an inclusion of not only the listed components it directly references, but also other non-specified components or elements.

The term 'substantially' or grammatical variations thereof refers to at least about 50%, for example 75%, 85%, 95% or 98%.

The terms 'oil', 'fat', 'grease' or 'wax' or grammatical variations thereof collectively referred to as 'sebum' are produced by sebaceous glands and refer to compounds that are at least moderately immiscible to completely immiscible in water and are characterised by having fatty acid groups.

The term 'transdermal' or grammatical variations thereof refers to the route of administration where an agent or agents are transported via diffusion through the epidermis layer of the skin and into the dermis layer to reach the microcirculation of the dermis.

The term 'vehicle' and grammatical variations refer to a therapeutically inactive formulation that may be mixed with one or more active agents and used to convey the active agent or agents.

The term 'therapeutically effective' with reference to an amount or dosage of a composition as described herein, refers to an amount of a composition and/or active compound which is sufficient to effectively treat a disorder or condition requiring treatment.

The term 'treat' or grammatical variations thereof refers to control of a disorder or disease including control or eradication of parasites on or within an animal.

In a first aspect there is provided a transdermal parasiticidal formulation in the form of a solution including a therapeutically effective amount of levamisole anthelmintic agent dissolved in a solution including isopropyl myristate and D-limonene.

The inventor has unexpectedly found that the above described combination of isopropyl myristate and D-limonene as a solvent system stabilises levamisole in solution for long periods of time without an appreciable change in levamisole activity and avoids any separation and/or sedimentation. This may be useful as it enables manufacturing to be completed in multiple steps, the first being a stabilisation step and subsequent storage of the 'stock' or 'base' levamisole solution in preparation for later smaller batch production of transdermal formulations such as those noted further below. Alternatively, the formulation described may be used as is, or with a diluent or other compounds.

Levamisole may be present, the highest concentration of levamisole being defined by the point at which the levamisole shifts from being soluble to being insoluble in the formulation. For the purposes of this specification, the term 'insoluble' in context of levamisole concentration refers to the levamisole no longer fully dissolving into the solution and separating into a separate phase and/or forming undissolved droplets. Levamisole may be present in sufficient quantities in an amount of at least 0.1% w/v of the total solution. Levamisole may be present in sufficient quantities to be diluted in further manufacturing and still provide about 0.1, or 0.2, or 0.3, or 0.4, or 0.5, or 0.6, or 0.7, or 0.8, or 0.9, or 1.0, or 1.5, or 2.0, or 2.5, or 3.0, or 3.5, or 4.0, or 4.5, or 5.0, or 5.5, or 6.0, or 6.5, or 7.0, or 7.5, or 8.0, or 8.5, or 9.0, or 9.5, 10% w/v of the total end formulation. In one embodiment, the levamisole may be present in sufficient quantities to be diluted in further manufacturing and still provide about 0.1 to 10% w/v of the total end formulation.

Isopropyl myristate was identified by the inventor as an excellent solvent with good solubilising characteristics particularly for levamisole powder. D-Limonene was found to add a high degree of stability to the formulation preventing any crystallisation occurring during storage plus no degradation of the levamisole activity was noted once stabilised as described. Both compounds also confer other properties once example being the penetrating activity of the isopropyl myristate.

Isopropyl myristate and D-limonene may be present in total at a rate of 1, or 2, or 3, or 4, or 5, or 6, or 7, or 8, or 9, or 10, or 11, or 12, or 13, or 14, or 15, or 16, or 17, or 18, or 19, or 20, or 21, or 22, or 23, or 24, or 25, or 30, or 35, or 40, or 45, or 50, or 55% w/v of the total formulation. In one embodiment, isopropyl myristate and D-limonene may be present in total at a rate of 1-55% w/v of the total formulation. The molar ratio of isopropyl myristate to D-limonene may be from about 10:1, or 11:1, 12:1, or 13:1, or 14:1, or 15:1. The molar ratio of isopropyl myristate to D-limonene may be from about 10:1 to about 15:1. These ratios and concentrations in the inventor's experience maximises the solubility of the levamisole in the solvent solution and confers the ideal stability.

The above formulation may further include a therapeutically effective amount of at least one additional macrocyclic lactone compound as an active anthelmintic agent. In one embodiment the macrocyclic lactone compound may be selected from: abamectin, moxidectin, eprinomectin, selamectin, ivermectin, milbemycins, and combinations thereof. The formulation may include 0.1, or 0.2, or 0.3, or 0.4, or 0.5, or 0.6, or 0.7, or 0.8, or 0.9, or 1, or 1.5, or 2, or 2.5, or 3, or 3.5, or 4, or 4.5, or 5, or 5.5, or 6, or 6.5, or 7, or 7.5, or 8, or 8.5, or 9, or 9.5, or 10% w/v macrocyclic lactone(s) in the total formulation. The formulation may include 0.1 to 10% w/v macrocyclic lactone(s) in the total formulation.

The above noted macrocyclic lactone may be dissolved in a further solvent. The solvent may be selected from one or more diethylene glycol ether (DGE) compounds. The solvent may be a DGE compound selected from: diethylene glycol monobutyl ether, diethylene glycol monoethyl ether, diethylene glycol monomethyl ether and combinations thereof. The solvent(s) may be present at a total concentration of about 30, or 35, or 40, or 45, or 50, or 55, or 60, or 65, or 70, or 75, or 80% w/v total composition. The solvent may be present at a total concentration of 30-70% w/v total composition. In one embodiment, diethylene glycol monoethyl ether may be used. DGE's are understood by the inventor to be useful as a solvent particularly when a macrocyclic lactone present. DGE's also only evaporate slowly meaning their solvent properties are maintained for longer. DGE's maintain the active agent, macrocyclic lactone, within the formulation and prevent dissolution of the agent into any fats, oils or waxes that may be present approximate the skin of an animal.

The formulation may include at least one penetrating agent or agents selected from at least one non-ionic surfactant. It may be appreciated that isopropyl myristate itself may act as a transdermal agent however it may be useful to add additional transdermal agents. In the inventor's experience, non-ionic surfactants are a useful choice as penetrating agent(s). The transdermal penetration agent or agents may be selected from EO/PO block co-polymers, alcohol ethoxylates, cocamide diethanolamine (DEA) and combinations thereof. The above described transdermal agents increase the pore size of the skin and sebum allowing the formulation and/or agent or agents to pass through the skin barrier. These agents may also be particularly useful as they may aid dissolution of any sebum oils, waxes or fats present at the site of administration thereby removing these barriers to diffusion. The transdermal agent or agents may be present at a concentration of 0.1, or 0.2, or 0.3, or 0.4, or 0.5, or 0.6, or 0.7, or 0.8, or 0.9, or 1, or 2, or 3, or 4, or 5, or 6, or 7, or 8, or 9, or 10, or 11, or 12, or 13, or 14, or 15, or 16, or 17, or 18, or 19, or 20% w/v of total formulation. The transdermal agent or agents may be present at a concentration of 0.1 to 20% w/v. The transdermal agent or agents may be present at a concentration of 5 to 15% w/v. The transdermal agent or agents may be present at a concentration of 5 to 12% w/v. The transdermal agents may also act as surfactants and/or wetting agents in the above described formulation thereby minimising the number of excipients required.

The formulation may further include at least one preservative. The preservative may be at least one alcohol. Examples of alcohols that may be used as preservatives include benzyl alcohol, chlorobutanol, phenylethyl alcohol, ethyl alcohol and combinations thereof. Where used, the preservative may be present in an amount from 0.1, or 0.2, or 0.3, or 0.4, or 0.5, or 0.6, or 0.7, or 0.8, or 0.9, or 1.0, or 1.1, or 1.2, or 1.3, or 1.4, or 1.5, or 1.6, or 1.7, or 1.8, or 1.9, or 2.0, or 2.1, or 2.2, or 2.3, or 2.4, or 2.5, or 2.6, or 2.7, or 2.8, or 2.9, or 3.0, or 3.1, or 3.2, or 3.3, or 3.4, or 3.5, or 3.6, or 3.7, or 3.8, or 3.9, or 4.0, or 4.1, or 4.2, or 4.3, or 4.4, or 4.5, or 4.6, or 4.7, or 4.8, or 4.9, or 5.0 w/v of the total formulation. The preservative may be present at a concentration of about 0.1 to 5.0% w/v of total formulation. The preservative may be present at a concentration of about 0.5 to 5.0% w/v of total formulation. Besides the stabilising effects of alcohols, the inventor has also found that alcohols may also enhance the transdermal properties of the formulation when lanolin is present about the area of administration. Lanolin present in woolly animals is highly repellent to transdermal formulations primarily due to the hydrophobicity or fatty acids present in the lanolin. Alcohols may act to shift the equilibrium dramatically in the conversion of fatty acid or hydroxyl groups on the lanolin molecule into esters with aryl groups. While this reaction may occur anyway without alcohols present, the reaction speed is slow and hence does not assist or only minimally assists with transdermal penetration. Addition of alcohols may dramatically change the equilibrium in favour of esterification resulting in greatly enhanced transdermal penetration as the esterified lanolin acts like a soap encouraging transfer through the epidermis rather than the repellent effects of fatty acids. By way of further explanation, esters act as surfactants and wetting agents hence the converted lanolin aids transdermal transfer.

The formulation may further include at least one diluent. The diluent may be selected from one or more glycol compounds. Examples of glycols that may be used include: propylene glycol compounds and/or ethylene glycol compounds. Such diluents may be useful due to their humectant properties and may also have emollient properties as well. In addition, such carriers may assist by preventing skin dryness at the site of administration. The humectant carrier may be added to volume (q.v.) and does not require any specific concentration but for example, may be present at a concentration of 5, or 10, or 15, or 20, or 25, or 30, or 35, or 40, or 45, or 50% w/v of total composition. The diluent may be present at a concentration of 5 to 50% w/v. The diluent may be present at a concentration of 10 to 20% w/v.

The above formulation may be administered to a woolly animal. The above formulation has significant advantages over many art formulations when administered to woolly animals or animals with a skin layer that includes sebum fats, oils or waxes, one example being sheep. The inventor has found that on administration, the above formulation diffuses the active agent or agents present in the formulation through the epidermis layer and at least partly, dissolves or penetrates sebum barrier fats, oils, waxes or greases present at the administration site. Excellent penetration occurs as measured in trials completed by the inventor. It is even possible to visually observe the diffusion process taking place with the formulation appearing to dissolve any fats, oils or waxes present. The inventor has also found and shown in experiments that the formulation may be administered to the back of a woolly animal such as a sheep without needing to prepare the site of administration in any way—the site need not be freshly shorn or cleaned. The formulation is able to penetrate through any dirt or fat, oils or waxes present. The formulation is also sufficient labile to diffuse down any woolly hairs presents and then into the skin layer. As may be appreciated, diffusion in such environments is a major challenge as the skin layer is difficult to reach from wool, dirt, and for sheep, a tough and repellent lanolin layer. The above formulations in fact use lanolin to help with diffusion by converting lanolin at the administration site chemically to an ester form that assists diffusion.

The final formulation viscosity may be less than or equal to 5000 cps, or 4500 cps, or 4000 cps, or 3500 cps, or 3000 cps, or 2500 cps, or 2000 cps. The viscosity may be less than or equal to 2000 cps. The inventor has found that the formulation described herein is easy to handle such as when pouring the formulation or when delivering in spot form. A lower viscosity and low shear rates means easier mixing for less energy input during manufacture and less force being required to administer the formulation and more accurate measuring of required dose. Having to exert large amounts of energy in order to mix the formulation or pour/spot on administration is not ideal as, besides added labour or energy costs, mixing may not be as complete as desired. A lower viscosity particularly at low energy inputs is preferable.

The formulation may include at least one further active compound. In one embodiment, the at least one further active compound may be a compound with endo-parasiticidal and/or ecto-parasiticidal activity. The active may be one or more insecticides. The insecticides may be selected from one or more of the following compounds: triflumuron, diflubenzuron, cyromazine, or at least one compound selected from the group of pyrethroid compounds. Where further actives are added, they may be added directly to the base formulation or dissolved in a solvent prior to dissolution in the base formulation above. In one embodiment, additional actives, if used, may comprise less or equal to 20%, or 19%, or 18%, or 17%, or 16%, or 15%, or 14%, or 13%, or 12%, or 11%, or 10%, or 9%, or 8%, or 7%, or 6%, or 5%, or 4%, or 3%, or 2%, or 1% w/v/of the total formulation. The amount may be less than 20% w/v.

Other formulation aids, such as colouring agents, additional antimicrobials, buffering agents, pH adjusters and antifoaming agents may also be added depending on the end application or desired characteristics. These aids are preferably non-toxic and complementary to transdermal administration.

In a second aspect, there is provided a transdermal parasiticidal formulation in the form of a solution including:

(a) a therapeutically effective amount of levamisole anthelmintic agent dissolved in a solution including isopropyl myristate and D-limonene;
(b) at least one solvent selected from one or more diethylene glycol ether (DGE) compounds;
(c) a penetrating agent or agents selected from at least one non-ionic surfactant;
(d) at least one preservative; and
(e) at least one diluent.

In a third aspect there is provided a dual active anthelmintic formulation formulated for transdermal administration including:

(a) a therapeutically effective amount of levamisole anthelmintic agent dissolved in a solution including isopropyl myristate and D-limonene;
(b) a therapeutically effective amount of a macrocyclic lactone dissolved in at least one diethylene glycol ether (DGE) compound;
(c) a penetrating agent or agents selected from at least one non-ionic surfactant;
(d) at least one preservative; and
(e) at least one diluent.

In a fourth aspect there is provided a method of treatment of a condition and/or disease in an animal by administration of a composition substantially as described above.

In a fifth aspect there is provided the use of a formulation substantially as described above along with at least one active agent in the manufacture of a composition formulated for transdermal administration in the treatment of a condition and/or disease.

In the above aspects, the animal may be a non-human animal. The non-human animal may be a woolly species of animal. Examples of animals particularly well suited to use of the described formulation include sheep or lambs, goats, rabbits, alpaca and llama. The animal may also be a non-woolly species, examples including cattle and deer.

In the above methods and uses, the transdermal formulation may be stored in a tube or plunger for an extended period of time without risk of separation or other changes in the product that might impact on stability.

Further, the formulations may be applied via readily available applicators such as drench guns or other spray systems or simply directly from a syringe or tube. The ability to use existing forms of applicator was unexpected—art formulations often require proprietary administrations devices to be used. In the present case, the inventor found that the formulation efficacy does not depend on application technique, unlike prior art compositions.

In the above aspects, the method of administration may be by applying the composition to the back of an animal. Administration may be as a stripe or stripes ('pour on'). Administration may be as a spot or spots ('spot on'). A 'stripe' refers to a strip along part or all of the length of the back of an animal. A 'spot' refers to a localised area of application, generally approximately circular in shape. As may be appreciated, one draw back of pour on formulations is that they are generally applied as a stripe or two stripes typically running from the back of neck of animal through to the rump. This requires a moderate volume of formulation and requires uninterrupted application, which is complicated due to the animal moving during application or due to the operator not being used for the full length. Spot on application by the present formulation resolves the above issues related to pour on formulations since only one or more spots need be applied and these need not be in any uniform location.

One advantage of the transdermal formulation described herein is that no special preparation of the administration site is required since the formulation is able to diffuse through any dirt or fats, oils or waxes that may be present on the skin. Further, it is not necessary to directly apply the composition to the skin layer itself and instead the formulation may be applied to animal wool or fur. The formulation is sufficiently labile and slow to evaporate to allow diffusion and movement along any fibres such as wool or fur that may be present.

In summary, advantages of the formulations, methods of treatment, and uses thereof should be apparent including the ability to penetrate the epidermis in an effective manner even when the skin is covered by barriers such as wool, dirt and sebum oils, waxes, fats. A yet further advantage is that the formulation described maintains a viscosity sufficiently low to allow for accurate administration by pouring or spot application of the formulation to an animal.

As noted in the background section, existing products contain inherent problems or difficulties limiting their use. The above described formulation may be used at any stage of wool growth and hence does not have any limits on application time such as around shearing. No special applicator is required for delivery. The above formulation is an organic solvent formulation so is physiologically acceptable. Finally, the above formulation has the considerable advantage of being able to be spot applied thereby reducing the risk of varying dosages and minimising the volume of formulation needed.

The embodiments described above may also be said broadly to consist in the parts, elements and features referred to or indicated in the specification of the application, individually or collectively, and any or all combinations of any two or more said parts, elements or features, and where specific integers are mentioned herein which have known equivalents in the art to which the embodiments relates, such known equivalents are deemed to be incorporated herein as of individually set forth, Where specific integers are mentioned herein which have known equivalents in the art to which this invention relates, such known equivalents are deemed to be incorporated herein as if individually set forth.

WORKING EXAMPLES

The above described formulations, methods of treatment and uses thereof are now described by reference to specific examples.

Example 1

A levamisole formulation in the form of a solution is described below in Table 1:

TABLE 1

| Example Formulation | |
|---|---|
| Compound | Amount (w/v) |
| Levamisole | 3% |
| Isopropyl myristate | 90% |
| D-limonene | 7% |

Example 2

The formulation of Example 1 may be made by measuring out and mixing together the levamisole (typically in the form of a powder) into the liquid isopropyl myristate and D-limonene and agitating the mixture for 30 seconds to an hour to ensure full dissolution occurs. The resulting formulation may be used for further formulating or stored in this form with no risk of loss in stability such as by levamisole degradation or crystallisation.

Example 3

An example of a levamisole transdermal formulation is described below in Table 2:

TABLE 2

| Example Formulation | |
|---|---|
| Compound | Amount (w/v) |
| Diethylene glycol monobutyl ether (DGBE) | 40-55% |
| Diethylene glycol monoethyl ether (DEGEE) | 10-15% |
| Levamisole base solution in isopropyl myristate/D-limonene | 10-25% equivalent to 0.05 to 1% levamisole in the total solution |
| Benzyl alcohol | 0.1-5% |
| Ethylene glycol-propylene glycol block co-polymer | 5-10% |
| Monopropylene glycol | To volume q.v. |

Example 4

An alternative formulation is described below in Table 3 containing both levamisole and a macrocyclic lactone:

TABLE 3

| Example Formulation | |
|---|---|
| Compound | Amount (w/v) |
| Diethylene glycol monobutyl ether (DGBE) | 40-55% |
| Macrocyclic lactone | 0.1-5% |
| Levamisole base solution in isopropyl myristate/D-limonene | 10-25% equivalent to 0.05 to 1% levamisole in the total solution |
| Phenylethyl alcohol | 0.1-5% |
| Ethylene glycol-propylene glycol block co-polymer | 5-10% |
| Monopropylene glycol | To volume q.v. |

Example 5

An example transdermal formulation to deliver abamectin and levamisole is described below in Table 4:

TABLE 4

| Example Formulation | |
|---|---|
| Compound | Amount (w/v) |
| Abamectin | 0.4-1% |
| Diethylene glycol monobutyl ether (DGBE) | 40-55% |
| Levamisole base solution in isopropyl myristate/D-limonene | 10-25% equivalent to 0.05 to 1% levamisole in the total solution |
| Benzyl alcohol | 0.5-2% |
| Ethylene glycol-propylene glycol block co-polymer | 0.1-0.5% |
| Monopropylene glycol | To volume (anticipated concentration approximately 10-40%) |

Example 6

An example transdermal formulation to deliver moxidectin and levamisole is described below in Table 5:

TABLE 5

| Example Formulation | |
|---|---|
| Compound | Amount (w/v) |
| Moxidectin | 0.2-1% |
| Diethylene glycol monobutyl ether (DGBE) | 40-55% |
| Levamisole base solution in isopropyl myristate/D-limonene | 10-25% equivalent to 0.05 to 1% levamisole in the total solution |
| Ethyl alcohol | 0.5-2% |
| Ethylene glycol-propylene glycol block co-polymer | 0.1-0.5% |
| Monopropylene glycol | To volume (anticipated concentration approximately 10-40%) |

Example 7

An example transdermal formulation to deliver abamectin and levamisole is described below in Table 6:

TABLE 6

| Example Formulation | |
|---|---|
| Compound | Amount (w/v) |
| Abamectin | 0.4-1% |
| Diethylene glycol monobutyl ether (DGBE) | 40-55% |
| Levamisole base solution in isopropyl myristate/D-limonene | 10-25% equivalent to 0.05 to 1% levamisole in the total solution |
| Chlorobutanol | 0.5-2% |
| Ethylene glycol-propylene glycol block co-polymer | 0.1-0.5% |
| Ethylene glycol | 10% |
| Propylene glycol | To volume of about 10-30% |

Example 8

An example transdermal formulation to deliver abamectin and levamisole is described below in Table 7:

TABLE 7

| Example Formulation | |
|---|---|
| Compound | Amount (w/v) |
| Abamectin | 0.4-1% |
| Levamisole base solution in isopropyl myristate/D-limonene | 50% equivalent to 0.05 to 1% levamisole in the total solution |
| Ethyl alcohol | 0.2% |
| EO/PO block copolymers | 0.1-0.5% |
| Diethylene glycol monoethyl ether | 40% |
| Ethylene glycol-propylene glycol block co-polymer | 0.1-0.5% |
| Propylene glycol | To volume of about 8.3-9.6% |

Example 9

An example transdermal formulation to deliver moxidectin and levamisole is described below in Table 8:

TABLE 8

| Example Formulation | |
|---|---|
| Compound | Amount (w/v) |
| Moxidectin | 0.2-0.6% |
| Levamisole base solution in isopropyl myristate/D-limonene | 55% equivalent to 5 to 6% levamisole in the total solution |
| Phenyl ethyl alcohol | 0.1% |
| EO/PO block copolymers | 0.3% |
| Diethylene glycol monobutyl ether | 40% |
| Propylene glycol | 4% |

Example 10

An example transdermal formulation to deliver abamectin and levamisole is described below in Table 9:

TABLE 9

| Example Formulation | |
|---|---|
| Compound | Amount (w/v) |
| Abamectin | 0.6% |
| Levamisole base solution in isopropyl myristate/D-limonene | 35% equivalent to 0.2-0.5% levamisole in the total solution |
| Ethyl alcohol | 0.2% |
| EO/PO block copolymers | 0.5% |
| Diethylene glycol monoethyl ether | 40% |
| Propylene glycol | To volume approximately 23.7% |

Example 11

A method of manufacturing the products described in Examples 4 to 10 may be via the following steps:

(a) Prepare a solution of levamisole in isopropyl myristate and D-limonene;

(b) Add required amount of diethylene glycol ether and macrocyclic lactone e.g. abamectin or moxidectin;

(c) Mixing until the macrocyclic lactone is dissolved;

(d) Add preservative and penetrating agent and bringing to volume by using glycols.

Example 12

The efficacy of the formulation was tested using composition with double active ingredients levamisole and abamectin as agents.

The formulation was administered via a plunger at the calculate dose to the backs of sheep as two separate spots ('spot on' treatment) of approximately 20 ml each at the back of the neck and about the rump of the animal (n=25 sheep). No cleaning or special pre-treatment of the wool or skin occurred prior to administration. The sheep had not been sheared prior to treatment and represented a difficult challenge for transdermal delivery due to the long wool coating (approximately 3 inches long), dirt and sebum oil/wax/grease layer on the animal skin, mainly being lanolin.

Results are shown in Table 10 below of the faecal egg count (measured in eggs per gram) before administration and 11 days post administration:

TABLE 10

| Efficacy Trial Results | | | |
|---|---|---|---|
| Sheep Mob Number (n = 25 total) | Faecal Egg Count Before Administration [eggs per gram] | Faecal Egg Count at Day 11 Post Administration [eggs per gram] | Faecal Egg Count at Day 15 Post Administration [eggs per gram] |
| Sample A | 45 | 0 | 0 |
| Sample B | 90 | 0 | 0 |
| Sample C | 0 | 0 | 0 |
| Sample D | 660 | 0 | 0 |

Example 13

The efficacy of the formulation was tested using a formulation with levamisole and abamectin as agents.

The formulation was administered via a drench gun used for power drenching of sheep, at the calculate dose to the backs of sheep as two separate spots of approximately 20 ml each at the back of the neck and about the rump of the animal (n=55 sheep). No cleaning or special pre-treatment of the wool or skin occurred prior to administration. The sheep had not been sheared prior to treatment and represented a difficult challenge for transdermal delivery due to the long wool coating (more than 3 inches long), dirt and sebum oil/wax/grease layer on the animal skin, mainly being lanolin.

Readings were taken on 11, 17 and 24 days of post treatment.

Results are shown in Table 8 below of the faecal egg count (measured in eggs per gram) before administration and 11, 17, 24 days post administration:

TABLE 11

Efficacy Trial Results monitored for 24 days post-application

| Sheep Mob Number (n = 25 total) | Faecal Egg Count Before Administration [eggs per gram] | Faecal Egg Count at Day 11 Post Administration [eggs per gram] | Faecal Egg Count at Day 17 Post Administration [eggs per gram] | Faecal Egg Count at Day 24 Post Administration [eggs per gram] |
|---|---|---|---|---|
| Sample | 300 | 0 | 0 | 0 |

As can be seen from the above, the results were positive with a complete removal of the parasite infection thereby showing that excellent transdermal transfer had occurred.

Aspects of the formulations, methods of treatment and uses thereof have been described by way of example only and it should be appreciated that modifications and additions may be made thereto without departing from the scope of the claims herein.

What is claimed is:

1. A formulation comprising a therapeutically effective amount of levamisole anthelmintic agent dissolved in a solution comprising isopropyl myristate and D-limonene, wherein the formulation is suitable for transdermal administration.

2. The formulation of claim 1, wherein the levamisole anthelmintic agent is fully dissolved.

3. The formulation of claim 1, wherein the isopropyl myristate and D-limonene, taken together, are 1-55% w/v of the formulation.

4. The formulation of claim 1, wherein the molar ratio of isopropyl myristate to D-limonene is from about 10:1 to about 15:1.

5. The formulation of claim 1, further comprising one or more macrocyclic lactone compounds.

6. The formulation of claim 5, wherein the one or more macrocyclic lactone compounds are independently selected from the group consisting of abamectin, moxidectin, eprinomectin, selamectin, ivermectin, and milbemycins.

7. The formulation of claim 5, wherein the one or more macrocyclic lactone compounds, taken together, are 0.1 to 10% w/v of the composition.

8. The formulation of claim 1, further comprising one or more solvents independently selected from the group consisting of diethylene glycol ether (DGE) compounds.

9. The formulation of claim 8, wherein the one or more DGE compounds are independently selected from the group consisting of diethylene glycol monobutyl ether, diethylene glycol monoethyl ether, and diethylene glycol monomethyl ether.

10. The formulation of claim 8, wherein the solvent is 30-70% w/v of the formulation.

11. The formulation of claim 1, wherein the formulation further comprises one or more transdermal penetrating agents independently selected from the group consisting of non-ionic surfactants.

12. The formulation of claim 11, wherein the one or more transdermal penetrating agents are independently selected from the group consisting of EO/PO block co-polymers, alcohol ethoxylates, and cocamide diethanolamine.

13. The formulation of claim 11, wherein the one or more transdermal penetrating agents, taken together, are 0.1 to 20% w/v of the formulation.

14. The formulation of claim 1, wherein the formulation further comprises one or more preservatives.

15. The formulation of claim 14, wherein the one or more preservatives are independently selected from the group consisting of benzyl alcohol, chlorobutanol, phenylethyl alcohol, and ethyl alcohol.

16. The formulation of claim 14, wherein the one or more preservatives, taken together, are about 0.1 to 5.0% w/v of the formulation.

17. The formulation of claim 1, wherein the formulation further comprises one or more diluents.

18. The formulation of claim 17, wherein the one or more diluents are independently selected from the group consisting of glycol compounds.

19. The formulation of claim 17, wherein the one or more diluents are independently selected from the group consisting of propylene glycol and ethylene glycol.

20. The formulation of claim 17, wherein the one or more diluents, taken together, are 5 to 50% w/v of the formulation.

21. The formulation of claim 1, wherein the viscosity of the formulation is less than or equal to 5000 cps.

22. The formulation of claim 1, wherein the formulation further comprises one or more additional active compounds.

23. The formulation of claim 22, wherein the one or more additional active compounds are independently selected from the group consisting of an endo-parasiticide, ecto-parasiticide, or insecticide.

24. The formulation of claim 23, wherein each insecticide is independently selected from the group consisting of triflumuron, diflubenzuron, cyromazine, and pyrethroid compounds.

25. The formulation of claim 22, wherein the one or more additional active compounds, taken together, are equal to or less than 20% w/v of the formulation.

26. A method of treating an endo-parasite or ecto-parasite infestation, comprising topically administering a therapeutically effective amount of the formulation of claim 1 to a non-human animal in need thereof.

27. The method of claim 26, wherein the formulation is administered as a pour on stripe or stripes.

28. The method of claim 26, wherein the formulation is administered as a spot or spots.

29. The method of claim 26, wherein the non-human animal is a woolly animal.

30. A dual active anthelmintic formulation, comprising:

a) a therapeutically effective amount of levamisole anthelmintic agent dissolved in a solution comprising isopropyl myristate and D-limonene;

b) a therapeutically effective amount of one or more macrocyclic lactone compounds dissolved in one or more diethylene glycol ether (DGE) compounds;

c) one or more penetrating agents independently selected from the group consisting of non-ionic surfactants;

d) one or more preservatives; and e) one or more diluents;

wherein the dual active anthelmintic formulation is suitable for transdermal administration.

* * * * *